US008227644B2

(12) United States Patent
Johnston et al.

(10) Patent No.: US 8,227,644 B2
(45) Date of Patent: *Jul. 24, 2012

(54) DIRECT AND SELECTIVE PRODUCTION OF ACETALDEHYDE FROM ACETIC ACID UTILIZING A SUPPORTED METAL CATALYST

(75) Inventors: Victor J. Johnston, Houston, TX (US); Barbara F. Kimmich, League City, TX (US); Jan Cornelis van der Waal, Delft (NL); James H. Zink, League City, TX (US); Virginie Zuzaniuk, Krommenie (NL); Josefina T. Chapman, Houston, TX (US); Laiyuan Chen, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/163,236

(22) Filed: Jun. 17, 2011

(65) Prior Publication Data

US 2011/0251435 A1    Oct. 13, 2011

Related U.S. Application Data

(63) Continuation of application No. 12/883,989, filed on Sep. 16, 2010, now Pat. No. 7,994,368, which is a continuation of application No. 12/221,135, filed on Jul. 31, 2008, now Pat. No. 7,816,565.

(51) Int. Cl.
*C07C 45/11* (2006.01)
*B01J 23/40* (2006.01)

(52) U.S. Cl. .......................... 568/484; 568/489; 502/326

(58) Field of Classification Search .................. 568/484, 568/489; 502/326
See application file for complete search history.

(56) References Cited

U.S. PATENT DOCUMENTS

| 2,105,540 A | 1/1938 | Lazier |
|---|---|---|
| 2,882,244 A | 4/1959 | Milton |
| 3,130,007 A | 4/1964 | Breck |
| 3,702,886 A | 11/1972 | Argauer et al. |
| 4,018,514 A | 4/1977 | Plummer |
| 4,328,373 A | 5/1982 | Strojny |
| 4,398,039 A | 8/1983 | Pesa et al. |
| 4,421,939 A | 12/1983 | Kiff et al. |
| 4,443,639 A | 4/1984 | Pesa et al. |
| 4,480,115 A | 10/1984 | McGinnis |
| 4,550,185 A | 10/1985 | Mabry et al. |
| 4,613,700 A | 9/1986 | Maki et al. |
| 4,777,303 A | 10/1988 | Kitson et al. |
| 4,804,791 A | 2/1989 | Kitson et al. |
| 4,990,655 A | 2/1991 | Kitson et al. |
| 5,008,235 A | 4/1991 | Wegman et al. |
| 5,059,716 A * | 10/1991 | Joentgen et al. ............. 568/435 |
| 5,137,861 A | 8/1992 | Shih et al. |
| 5,149,680 A | 9/1992 | Kitson et al. |
| 5,243,095 A | 9/1993 | Roberts et al. |
| 5,306,845 A | 4/1994 | Yokohama et al. |
| 5,334,769 A | 8/1994 | Ferrero et al. |
| 5,350,504 A | 9/1994 | Dessau |
| 5,476,827 A | 12/1995 | Ferrero et al. |
| RE35,377 E | 11/1996 | Steinberg et al. |
| 5,821,111 A | 10/1998 | Grady et al. |
| 5,945,570 A | 8/1999 | Arhancet et al. |
| 6,049,008 A | 4/2000 | Roberts et al. |
| 6,121,498 A | 9/2000 | Tustin et al. |
| 6,232,352 B1 | 5/2001 | Vidalin |
| 6,294,703 B1 | 9/2001 | Hara et al. |
| 6,486,366 B1 | 11/2002 | Ostgard et al. |
| 6,495,730 B1 | 12/2002 | Konishi et al. |
| 6,657,078 B2 | 12/2003 | Scates et al. |
| 6,685,754 B2 | 2/2004 | Kindig et al. |
| 7,084,312 B1 | 8/2006 | Huber et al. |
| 7,425,657 B1 | 9/2008 | Elliott et al. |
| 7,538,060 B2 | 5/2009 | Barnicki et al. |
| 7,608,744 B1 | 10/2009 | Johnston et al. |
| 7,816,565 B2 | 10/2010 | Johnston et al. |
| 7,863,489 B2 | 1/2011 | Johnston et al. |
| 7,884,253 B2 | 2/2011 | Stites et al. |
| 2007/0270511 A1 | 11/2007 | Melnichuk et al. |
| 2009/0221725 A1 | 9/2009 | Chorney et al. |
| 2009/0326080 A1 | 12/2009 | Chornet et al. |
| 2010/0168466 A1 | 7/2010 | Johnston et al. |

FOREIGN PATENT DOCUMENTS

| EP | 0372847 | 6/1990 |
|---|---|---|
| EP | 0285420 | 5/1991 |
| EP | 0539274 | 4/1993 |
| EP | 0953560 | 11/1999 |
| EP | 0990638 | 4/2000 |
| EP | 1262234 | 12/2002 |
| EP | 1277826 | 1/2003 |
| EP | 2060555 | 5/2009 |
| GB | 1168785 A | 10/1969 |
| GB | 2136704 A | 9/1984 |
| JP | 6-116182 | 4/1994 |
| JP | 11-147845 | 6/1999 |
| WO | WO 2005/102513 | 11/2005 |
| WO | WO 2009/063176 | 5/2009 |
| WO | WO 2009/086839 | 7/2009 |
| WO | WO 2010/014145 | 2/2010 |
| WO | WO 2010/014153 | 2/2010 |

OTHER PUBLICATIONS

International Search Report and Written Opinion for PCT/US2009/004187 mailed Mar. 24, 2010 (14 pages).
Pestman et al. (1997). Reactions of Carboxylic Acids on Oxides, *Journal of Catalysis 168*, 255-264.

(Continued)

*Primary Examiner* — Sikarl Witherspoon
(74) *Attorney, Agent, or Firm* — Roberts Mlotkowski Safran & Cole

(57) ABSTRACT

A process for the selective production of acetaldehyde by vapor phase reaction of acetic acid over a hydrogenating catalyst composition to form acetaldehyde is disclosed and claimed. In an embodiment of this invention reaction of acetic acid and hydrogen over platinum and iron supported on silica selectively produces acetaldehyde in a vapor phase at a temperature of about 300° C.

9 Claims, No Drawings

OTHER PUBLICATIONS

Pestman et al. (1998). Identification of the Active Sites in the Selective Hydrogenation of Acetic Acid to Acetaldehyde on Iron Oxide Catalysts, *Journal of Catalysis*, 174, 142-152.

Alcala et al. (2005). Experimental and DFT studies of the conversion of ethanol and acetic acid on PtSn-based catalysts, *Journal of Physical Chemistry*, 109(6), 2074-2085.

Zheng et al. (2007). Preparation and catalytic properties of a bimetallic Sn-Pt complex in the supercages of NaY zeolite by use of surface organometallic chemistry, *Applied Organometallic Chemistry*, 21(10), 836-840.

Santori et al. (2000). Hydrogenation of carbonylic compounds on $Pt/SiO_2$ catalysts modified with $SnBu_4$, *Studies in Surface Science and Catalysis*, 130, 2063-2068.

Proc. Roy Soc. A314, pp. 473-498 (1970).

Brunauer Emmett and Teller, J. Am. Chem. Soc. 60, 309 (1938).

Subramani et al., "A Review of Recent Literature to Search for an Efficient Catalytic Process for the Conversion of Syngas to Ethanol", Energy and Fuels 2008, 22, pp. 814-839.

Spivey et al., "Heterogeneous catalytic synthesis of ethanol from biomass-derived syngas", Chemical Society Reviews, 2007, 36, pp. 1514-1528.

Domine, et al., "Molecular Sieves", Society of Chemical Industry, London, 1968, 9 pages.

English language abstract for JP 6-116182, Apr. 26, 1994.

English language abstract for JP 11-147845, Feb. 6, 1999.

* cited by examiner

DIRECT AND SELECTIVE PRODUCTION OF ACETALDEHYDE FROM ACETIC ACID UTILIZING A SUPPORTED METAL CATALYST

CROSS REFERENCE TO RELATED APPLICATIONS

This application is a continuation of U.S. application Ser. No. 12/883,989, filed Sep. 16, 2010, which is a continuation of U.S. application Ser. No. 12/221,135, filed on Jul. 31, 2008, now U.S. Pat. No. 7,816,565, the entire contents and disclosures of which is hereby incorporated by reference.

FIELD OF THE INVENTION

The present invention relates generally to a process for the production of acetaldehyde from acetic acid. More specifically, the present invention relates to a process including hydrogenating acetic acid utilizing a supported metal catalyst, such as, for example, iron, platinum or ruthenium supported on a suitable catalyst support optionally including one or more additional hydrogenating metals to form acetaldehyde with high selectivity.

BACKGROUND

There is a long felt need for an economically viable process to convert acetic acid to acetaldehyde. Acetaldehyde is an important commodity feedstock for a variety of industrial products. For instance, acetaldehyde can readily be hydrogenated to ethanol, which in itself has wide variety of industrial applications including its wide utility as a gasoline additive. Acetaldehyde can also be converted to ethyl acetate by the Tischenko reaction or reacted with other compounds to form other products. Currently acetaldehyde is produced by the oxidation of ethylene, the Wacker oxidation of ethylene. Fluctuating natural gas and crude oil prices contribute to fluctuations in the cost of conventionally produced, petroleum or natural gas-sourced acetaldehyde, making the need for alternative sources of acetaldehyde all the greater when oil prices rise. Thus it is of interest to develop commercially viable routes to selectively hydrogenate acetic acid to acetaldehyde.

The catalytic hydrogenation of aromatic carboxylic acids to produce aromatic aldehydes has been reported in the literature. For instance, U.S.

U.S. Pat. No. 4,613,700 to Maki et al. discloses that aromatic aldehydes can be formed from aromatic carboxylic acids using a catalyst comprising zirconium oxide containing as an essential component at least one element selected from the group consisting of chromium, manganese, iron, cobalt, zinc, bismuth, lead rhenium and the elements of Group III in periods 3 to 6 of the periodic table. However, no examples of catalytic hydrogenation of aliphatic carboxylic acids such as acetic acid are provided in this disclosure.

U.S. Pat. No. 5,306,845 to Yokohama et al. discloses a method of producing an aldehyde, which comprises hydrogenating a carboxylic acid or its alkyl ester with molecular hydrogen in the presence of a catalyst containing chromium oxide of high purity having a specific surface area of at least 10 m$^2$/g and a total content of sodium, potassium, magnesium and calcium of not more than 0.4 weight percent. It is further reported therein that the hydrogenation reaction is conducted while maintaining the carboxylic acid or its alkyl ester at a concentration of not more than 10 volume percent. Additionally, the only example reported therein is hydrogenation of stearic acid to stearyl aldehyde. Most importantly, the selectivity to aldehyde drops significantly even if the total content of sodium, potassium, magnesium and calcium increases from about 0.3 weight percent to about 0.46 weight percent, thus rendering the process not suitable for a commercial operation.

U.S. Pat. No. 5,476,827 to Ferrero et al. describes a process for the preparation of aldehydes by catalytic hydrogenation of carboxylic acids, esters or anhydrides utilizing a bimetallic ruthenium/tin catalyst. The preferred carboxylic acids are the α-β-unsaturated carboxylic acids with an aromatic back bone or aromatic carboxylic acids. No examples of aliphatic carboxylic acids including acetic acid are provided.

U.S. Pat. No. 6,121,498 to Tustin et al. discloses a method for producing acetaldehyde from acetic acid. In this process, acetic acid is hydrogenated with hydrogen at an elevated temperature in the presence of an iron oxide catalyst containing between 2.5 and 90 weight percent palladium. However, the optimal condition reported therein is comprised of an iron oxide catalyst containing at least about 20 weight percent palladium, which affords about 80 percent selectivity to acetaldehyde with about 50 percent conversion of acetic acid. Additionally, significant amounts of by-products including methane, ethane, ethylene, ethanol and acetone are formed.

From the foregoing it is apparent that existing processes do not have the requisite catalysts to selectively convert acetic acid to acetaldehyde or existing art employs catalysts, which are either expensive and/or non-selective for the formation of acetaldehyde and produces undesirable by-products.

SUMMARY OF THE INVENTION

Surprisingly, it has now been unexpectedly found that acetaldehyde can be made on an industrial scale directly from acetic acid with very high selectivity and yield. More particularly, this invention provides a process for the selective formation of acetaldehyde from acetic acid comprising: hydrogenating acetic acid in the presence of hydrogen over a hydrogenating catalyst comprising at least one metal selected from the group consisting of iron, copper, gold, platinum, palladium and ruthenium supported on a suitable catalyst support. Optionally, the catalyst is further comprised of one or more metal catalysts selected from the group consisting of tin, aluminum, potassium, cobalt, molybdenum, tungsten and vanadium. More specifically, the catalyst suitable for the process of this invention is typically comprised of supported ruthenium alone or in combination with tin or iron; a supported iron alone or in combination with platinum or cobalt; or a combination of platinum and tin. Similarly, other catalysts suitable in the process of this invention include supported palladium alone or a combination of palladium/gold (Pd/Au) or palladium/copper (Pd/Cu), which can further comprise potassium acetate. Also suitable catalysts are a combination of palladium/iron (Pd/Fe), iron/cobalt (Fe/Co), copper/molybdenum (Cu/Mo) or copper/aluminum. Suitable catalyst supports include without any limitation, silica, alumina, calcium silicate, carbon, zirconia, zirconia-silica, titania, titania-silica, iron oxide and zeolite catalysts such as for example H-ZSM-5. Silica and iron oxide are particularly preferred catalyst supports in the process of this invention.

DETAILED DESCRIPTION OF THE INVENTION

The invention is described in detail below with reference to numerous embodiments for purposes of exemplification and illustration only. Modifications to particular embodiments within the spirit and scope of the present invention, set forth in the appended claims, will be readily apparent to those of skill in the art.

Unless more specifically defined below, terminology as used herein is given its ordinary meaning.

Typically, the catalyst metal loadings are expressed as weight percent of a catalyst metal based on the total dry weight of the metal and catalyst support. Thus, for example, one (1) weight percent of metal on a support means that one gram of pure metal is present in 100 grams of supported metal catalyst, i.e., the combined weight of support (99 grams) and the metal (1 gram).

"Conversion" is expressed as a mole percentage based on acetic acid in the feed. The conversion of acetic acid (AcOH) is calculated from gas chromatography (GC) data using the following equation:

$$\text{AcOH conversion (\%)} = 100 * \frac{\text{mmol AcOH in (feed stream)} - \text{mmol AcOH out } (GC)}{\text{mmol AcOH in (feed stream)}}$$

"Selectivity" is expressed as a mole percent based on converted acetic acid. For example, if the conversion is 50 mole % and 50 mole % of the converted acetic acid is converted to acetaldehyde (AcH), we refer to the acetaldehyde selectivity as 50%. Selectivity is calculated from gas chromatography (GC) data using the following equation:

$$\text{Selectivity to AcH (\%)} = 100 * \frac{\text{mmol AcH out } (GC)}{\frac{\text{Total mmol C out } (GC)}{2} - \text{mmol AcH out } (GC)}$$

wherein "Total mmol C out (GC)" refers to total mmols of carbon from all of the products analyzed by gas chromatograph.

The reaction proceeds in accordance with the following chemical equation:

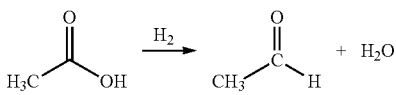

In accordance with the invention, conversion of acetic acid to acetaldehyde can be carried out in a variety of configurations, such as for example in a single reaction zone which may be a layered fixed bed, if so desired. An adiabatic reactor could be used, or a shell and tube reactor provided with a heat transfer medium could be used. The fixed bed can comprise a mixture of different catalyst particles or catalyst particles which include multiple catalysts as further described herein. The fixed bed may also include a layer of particulate material making up a mixing zone for the reactants. A reaction mixture including acetic acid, hydrogen and optionally an inert carrier gas is fed to the bed as a stream under pressure to the mixing zone. The stream is subsequently supplied (by way of pressure drop) to the reaction zone or layer. Reaction zone comprises a catalytic composition including a suitable hydrogenating catalyst where acetic acid is hydrogenated to produce acetaldehyde. Any suitable particle size may be used depending upon the type of reactor, throughput requirements and so forth.

Although various metal supported hydrogenating catalysts known to one skilled in the art can be employed in hydrogenating acetic acid to form acetaldehyde in the process of this invention it is preferred that the hydrogenating catalyst employed contains at least one or more metals selected from the group consisting of iron, copper, gold, platinum, palladium and ruthenium supported on a suitable catalyst support. Optionally, a second or third metal can be selected from the group consisting of tin, aluminum, potassium, cobalt, molybdenum, tungsten and vanadium. Preferably, the catalyst suitable for the process of this invention is comprised of ruthenium alone, supported on a suitable support such as iron oxide or silica or a combination of ruthenium and tin or ruthenium and iron supported on a suitable catalyst support. Similarly, the preferred hydrogenation catalyst is iron alone supported on a suitable support such as silica or a combination of iron and platinum or a combination of iron and cobalt supported on a suitable catalyst support such as silica. Similarly, other catalysts suitable in the process of this invention include supported palladium alone or a combination of palladium/gold (Pd/Au) or palladium/copper (Pd/Cu), which can further comprise potassium acetate. Also suitable catalysts are a combination of palladium/iron (Pd/Fe), iron/cobalt (Fe/Co), copper/molybdenum (Cu/Mo) or copper/aluminum.

Typically, when bimetallic catalysts are employed it is preferred that a suitable weight ratio of a combination of metals on a suitable support can be used as a hydrogenating catalyst. Thus, for example, a combination of ruthenium and iron (Ru/Fe), ruthenium and tin (Ru/Sn), palladium/copper (Pd/Cu), palladium/iron (Pd/Fe) in the weight ratio of about 0.1-1 are particularly preferred. More preferably, a weight ratio of Ru/Fe or Ru/Sn or Pd/Cu or Pd/Fe is about 0.2-0.5 and most preferably the weight ratio of Ru/Fe or Ru/Sn or Pd/Cu or Pd/Fe is about 0.2. Similar weight ratios can be employed for a catalyst combination of platinum and iron Pt/Fe, i.e., a weight ratio of 0.1-1, preferably 0.2-0.5 and most preferably 0.2. When a combination of cobalt and iron (Co/Fe) or copper/molybdenum (Cu/Mo) or copper/aluminum (Cu/Al) supported on a suitable catalyst support is employed, the preferred weight ratio of Co/Fe or Cu/Mo or Cu/Al is in the range of 1 to 5. For instance, a combination of 17.4 weight percent of cobalt and 4.8 weight percent of iron supported on silica is commercially available. Similarly, a copper-aluminum catalyst is sold under the name of T-4489 by Sud Chemie.

When ruthenium alone or palladium alone or iron alone is used as the metal catalyst on a suitable support any loading level of ruthenium, palladium or iron can be employed so as to affect the selective hydrogenation of acetic acid to acetaldehyde. Typically, however, the ruthenium or palladium loading level can range from 0.5 weight percent to about 20 weight percent, preferably 1 weight percent to about 10 weight percent and most preferably 1 weight percent to about 5 weight percent. Generally when a noble metal such as ruthenium or palladium alone are employed in the process of this invention, 0.5 to 1 weight percent of catalyst metal may be sufficient to obtain the optimum catalytic benefit. Preferred catalyst supports for ruthenium or palladium are iron oxide or silica. Similarly, when iron alone is used as the metal catalyst, the loading level of iron can range from 1 weight percent to about 20 weight percent, preferably 2 weight percent to about 10 weight percent and most preferably 3 weight percent to about 8 weight percent. Preferred catalyst support for iron is silica.

When bimetallic catalysts employed are two noble metals such as palladium and gold then the metal loading of each of the noble metal loading is in the range of from about 0.5 weight percent to about 20 weight percent, preferably 1 weight percent to about 10 weight percent and most preferably 1 weight percent to about 5 weight percent. However, as already noted above, low loadings of about 0.5 weight percent or 1 weight percent of each of the noble metals, such as palladium or gold brings about optimum catalytic effect in the process of this invention.

Various catalyst supports known in the art can be used to support the catalysts of this invention. Examples of such supports include without any limitation, zeolite, such as H-ZSM-5, iron oxide, silica, alumina, titania, zirconia, magnesium oxide, calcium silicate, carbon, graphite and a mixture thereof. Preferred supports are silica and iron oxide. More preferably silica is used as a catalyst support in the process of this invention. It is also important to note that the higher the purity of silica, the better it is as a support. Various forms of commercially available silica supports can be used in this invention including high surface area silica (HSA silica) as well as low surface area silica (LSA silica).

In another aspect of the process of this invention, any of known zeolite catalysts can also be employed as a catalyst support. While any zeolite having a pore diameter of at least about 0.6 nm can be used, preferably employed among such zeolites are the catalyst supports selected from the group consisting of mordenites, ZSM-5, a zeolite X and a zeolite Y.

The preparation of large-pore mordenites is described, for example, in U.S. Pat. No. 4,018,514 and in Mol. Sieves. Pap. Conf., 1967, 78, Soc. Chem. Ind. London, by D. DOMINE and J. QUOBEX.

Zeolite X is described, for example, in U.S. Pat. No. 2,882,244 and zeolite Y in U.S. Pat. No. 3,130,007.

Various zeolites and zeolite-type materials are known in the art for the catalysis of chemical reactions. For example, U.S. Pat. No. 3,702,886, of Argauer, discloses a class of synthetic zeolites, characterized as "Zeolite ZSM-5", which are effective for the catalysis of various hydrocarbon conversion processes.

The zeolites suitable for the procedure of the invention can be in the basic form, in the partially or totally acidified form, or in the partially delaminated form.

Preferably, the zeolite catalyst support in the process of the present invention are in the protic form, characterized as "H-ZSM-5" or "H-mordenite" zeolites, which are prepared from a corresponding "ZSM-5" zeolite or "mordenite" zeolite by replacing most, and generally at least about 80% of the cations of the latter zeolite with hydrogen ions using techniques well-known in the art. These zeolite catalysts are essentially crystalline aluminosilicates or in the neutral form, a combination of silica and alumina in a well defined crystalline structure. In a particularly preferred class of zeolite catalysts for purposes of the present invention, the molar ratio of $SiO_2$ to $Al_2O_3$ in these zeolites is within the ratio of about 10 to 60.

In another aspect of this invention, ruthenium is supported on either silica or iron oxide. A combination of ruthenium and tin, iron alone or a combination of platinum and iron, iron and cobalt, iron and ruthenium, and platinum and tin are supported on a high purity, low surface area silica or high purity, high surface area silica using the procedures well known in the art or the procedures further described herein. Other preferred catalyst supports for platinum or ruthenium based metal catalysts are titania and zirconia.

As noted above, the loading levels of a combination of two metal catalysts are generally referenced with the content of main catalyst metal and the weight ratio of the combination. For instance, the weight ratio of Ru/Sn, Ru/Fe, Pt/Sn or Pt/Fe is in the range of about 0.1 to 2. Thus, when the weight ratio of Ru/Sn, Ru/Fe or Pt/Fe is 0.1, the amount of ruthenium or platinum can be 0.1 or 1 weight percent and thus 1 or 10 weight percent of tin or iron is present on the catalyst support. Preferably, the weight ratio of Ru/Sn, Ru/Fe, Pt/Sn or Pt/Fe is about 0.5, and thus the amount of ruthenium or platinum on the catalyst support can be either 0.5 or 1 weight percent and that of tin or iron is either one or two weight percent. More preferably, the weight ratio of Ru/Sn, Ru/Fe, Pt/Sn or Pt/Fe is one or 0.2. Thus the amount of ruthenium or platinum on a support is 0.5, one or two weight percent and that of tin or iron is also 0.5, one or two weight percent when the weight ratio is one. Similarly, when a weight ratio of Ru/Sn, Ru/Fe or Pt/Fe is 0.2, the amount of ruthenium or platinum on the support can be 0.5 or one weight percent and of tin or iron is either 2.5 or five weight percent.

The amount of third metal loading if present on a support is not very critical in this invention and can vary in the range of about 0.1 weight percent to about 10 weight percent. A metal loading of about 1 weight percent to about 6 weight percent based on the weight of the support is particularly preferred.

The metal impregnation can be carried out using any of the known methods in the art. Typically, before impregnation the supports are dried at 120° C. and shaped to particles having size distribution in the range of about 0.2 to 0.4 mm. Optionally, the supports may be pressed, crushed and sieved to a desired size distribution. Any of the known methods to shape the support materials into desired size distribution can be employed.

For supports having low surface area, such as, for example, alpha-alumina, the metal solutions are added in excess until complete wetness or excess liquid impregnation so as to obtain desirable metal loadings.

As noted above, the hydrogenation catalysts used in the process of this invention are generally bimetallic containing platinum/iron, ruthenium/tin, ruthenium/iron, iron/cobalt and so on. Generally, without intending to be bound by any theory, it is believed that one metal acts as a promoter metal and another metal is the main metal. For instance, in the instant process of the invention, of the above noted combinations respectively, platinum, ruthenium, and iron are considered as main metals for preparing hydrogenation catalysts of this invention. The other metals, tin with ruthenium and iron with cobalt, platinum or ruthenium are considered to be the promoter metals depending upon various reaction parameters including, but not limited to catalyst support employed, reaction temperature and pressure, etc. The catalysts may include other promoter metals, such as tungsten, vanadium, molybdenum, chromium or zinc.

The bimetallic catalysts are generally impregnated in two steps. Each impregnation step is followed by drying and calcination. The bimetallic catalysts may also be prepared by co-impregnation. In most cases, the impregnation may be carried out using metal nitrate solutions. However, various other soluble salts which upon calcinations release metal ions, can also be used. Examples of other suitable metal salts for impregnation include metal oxalate, metal hydroxide, metal oxide, metal acetate, ammonium metal oxide, such as ammonium heptamolybdate hexahydrate, metal acids, such as perrhenic acid solution, and the like.

Thus in one embodiment of this invention, there is provided a hydrogenation catalyst wherein the catalyst support is silica or iron oxide with ruthenium alone as the hydrogenation catalyst. In this aspect of the invention the metal loading of ruthenium can range from one (1) weight percent to about twenty (20) weight percent, preferably one to ten weight percent and most preferably one to five weight percent.

In another embodiment of this invention, there is provided a hydrogenation catalyst wherein the catalyst support is silica with iron alone as the hydrogenation catalyst. In this aspect of the invention the metal loading of iron can range from one (1) weight percent to about twenty (20) weight percent, preferably two to ten weight percent and most preferably three to eight weight percent of iron.

In another embodiment of this invention, there is provided a bimetallic loading of ruthenium and tin or platinum and tin. In this aspect of the invention, the loading of ruthenium or platinum is about 0.5 weight percent to about 2 weight percent and the loading of tin is about 2.5 weight percent to about 10 weight percent. Specifically, ruthenium/tin or platinum/tin loading levels of 1/1, 1/5, 0.5/5, and 0.5/2.5 weight percent on silica can be used.

In another embodiment of this invention, there is further provided a hydrogenation catalyst wherein the catalyst support is high purity, low surface area silica with a bimetallic loading of platinum and iron or ruthenium and iron. In this aspect of the invention, the loading of platinum or ruthenium is about 0.5 weight percent to about 2 weight percent and the loading of iron is about 4 weight percent to about 10 weight percent. Specifically, platinum/iron or ruthenium/iron loading levels of 1/1, 1/5, 0.5/5, and 0.5/2.5 weight percent on high purity, low surface area silica can be used. Other preferred supports in this aspect of the invention include H-ZSM-5, graphitized carbon, zirconia, titania, iron oxide, silica-alumina and calcium silicate.

In another embodiment of this invention, there is further provided a hydrogenation catalyst wherein the bimetallic catalyst is cobalt and iron supported on silica. In this aspect of the invention, the loading level of cobalt is about 12 weight percent to about 22 weight percent and of iron is from about 3 to 8 weight percent. Specifically, cobalt loading level of 17.4 weight percent and iron loading level of 4.8 weight percent supported on silica is commercially available.

In general, by the practice of this invention, acetic acid can selectively be converted to acetaldehyde at very high rates. The selectivity to acetaldehyde in general is very high and may be at least 60 percent. Under preferred reaction conditions, acetic acid is converted to acetaldehyde at a selectivity of at least 70 percent or more preferably at a selectivity of over 80 percent such as at least 90 percent.

The conversion of acetic acid using the catalysts of this invention is at least 10% and can be up to 40% with selectivity to acetaldehyde at least 60%, preferably 70% and most preferably 80%.

Generally, the active catalysts of the invention are the single metal or the bimetallic catalysts as described herein. More specifically, a bimetallic catalyst containing ruthenium and tin, ruthenium and iron, platinum and tin, platinum and iron, and cobalt and iron supported on silica with a ruthenium or platinum loadings of 0.5 to 1 weight percent and tin and iron loadings of 5 weight percent and cobalt loading of about 18 weight percent are preferred. In accordance with the practice of this invention, acetic acid can be converted using this catalyst at conversions of around 40% with acetaldehyde selectivity of at least 60%, more preferably selectivity to acetaldehyde of at least 80% can be achieved.

Similar conversions and selectivities are achieved using zirconia, graphite or titania as a support and with similar loadings of ruthenium, platinum, tin, iron and cobalt as described above. Other promoter metals can also be used in conjunction with ruthenium or platinum as noted above.

In another aspect of this invention it is also possible to obtain high levels of conversions in the order of at least 25% and high selectivity to acetaldehyde of at least about 80% using ruthenium or iron loading of one weight percent to about five weight percent on silica or iron oxide as catalyst supports. In this aspect of the invention, other preferred catalyst supports include graphitized carbon, titania, zirconia, silica-alumina and calcium silicate.

In another aspect of the process of this invention, the hydrogenation is carried out at a pressure just sufficient to overcome the pressure drop across the catalytic bed.

The reaction may be carried out in the vapor or liquid state under a wide variety of conditions. Preferably, the reaction is carried out in the vapor phase. Reaction temperatures may be employed, for example in the range of about 250° C. to about 350° C., preferably about 290° C. to about 310° C. The pressure is generally uncritical to the reaction and subatmospheric, atmospheric or superatmospheric pressures may be employed. In most cases, however, the pressure of the reaction will be in the range of about 5 to 30 atmospheres absolute, most preferably the pressure of reaction zone is in the range of about 8 to 20 atmospheres absolute.

Although the reaction consumes a mole of hydrogen per mole of acetic acid to produce a mole of acetaldehyde, the actual molar ratio of acetic acid to hydrogen in the feed stream may be varied between wide limits, e.g. from about 100:1 to 1:100. It is preferred however, that such ratio be in the range of about 1:20 to 1:2. More preferably, the molar ratio of acetic acid to hydrogen is about 1:5.

The raw materials used in connection with the process of this invention may be derived from any suitable source including natural gas, petroleum, coal, biomass and so forth. It is well known to produce acetic acid through methanol carbonylation, acetaldehyde oxidation, ethylene oxidation, oxidative fermentation, and anaerobic fermentation and so forth. As petroleum and natural gas have become more expensive, methods for producing acetic acid and intermediates such as methanol and carbon monoxide from alternate carbon sources have drawn more interest. Of particular interest is the production of acetic acid from synthesis gas (syngas) that may be derived from any suitable carbon source. U.S. Pat. No. 6,232,352 to Vidalin, the disclosure of which is incorporated herein by reference, for example, teaches a method of retrofitting a methanol plant for the manufacture of acetic acid. By retrofitting a methanol plant the large capital costs associated with CO generation for a new acetic acid plant are significantly reduced or largely eliminated. All or part of the syngas is diverted from the methanol synthesis loop and supplied to a separator unit to recover CO and hydrogen, which are then used to produce acetic acid. In addition to acetic acid, the process can also be used to make hydrogen which is utilized in connection with this invention.

U.S. Pat. No. RE 35,377 Steinberg et al., also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolyzed with additional natural gas to form synthesis gas. The syngas is converted to methanol which may be carbonylated to acetic acid. The method likewise produces hydrogen which may be used in connection with this invention as noted above. See also, U.S. Pat. No. 5,821,111 Grady et al., which discloses a process for converting waste biomass through gasification into synthesis gas as well as U.S. Pat. No. 6,685,754 Kindig et al., the disclosures of which are incorporated herein by reference.

The acetic acid may be vaporized at the reaction temperature, and then it can be fed along with hydrogen in undiluted state or diluted with a relatively inert carrier gas, such as nitrogen, argon, helium, carbon dioxide and the like.

Alternatively, acetic acid in vapor form may be taken directly as crude product from the flash vessel of a methanol carbonylation unit of the class described in U.S. Pat. No. 6,657,078 of Scates et al., the disclosure of which is incorporated herein by reference. The crude vapor product may be fed directly to the reaction zones of the present invention without the need for condensing the acetic acid and light ends or removing water, saving overall processing costs.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, between about 0.5 and 100 seconds.

Typically, the catalyst is employed in a fixed bed reactor e.g. in the shape of an elongated pipe or tube where the reactants, typically in the vapor form, are passed over or through the catalyst. Other reactors, such as fluid or ebullient bed reactors, can be employed, if desired. In some instances, it is advantageous to use the hydrogenation catalysts in conjunction with an inert material to regulate the pressure drop, flow, heat balance or other process parameters in the catalyst bed including the contact time of the reactant compounds with the catalyst particles.

In one of the preferred embodiments there is also provided a process for selective and direct formation of acetaldehyde from acetic acid comprising: contacting a feed stream containing acetic acid and hydrogen at an elevated temperature with a suitable hydrogenating catalyst containing about 0.5 weight percent to about 1 weight percent of platinum or ruthenium and about 2.5 weight percent to about 5 weight percent of tin or iron on a suitable catalyst support. Preferred catalyst support in this embodiment of the invention is silica.

In this embodiment of the process of this invention, the preferred hydrogenation catalyst contains about 0.5 weight percent or about one (1) weight percent platinum and about five (5) weight percent iron or tin; or about 0.5 weight percent or about one (1) weight percent ruthenium and about five (5) weight percent tin or iron. In this embodiment of the process of this invention, it is preferred that the hydrogenation catalysts are layered in a fixed bed and the reaction is carried out in the vapor phase using a feed stream of acetic acid and hydrogen in the molar range of about 1:20 to 1:5 and at a temperature in the range of about 290° C. to 310° C. and at a pressure of reaction zones in the range of about 8 to 20 atmospheres absolute, and the contact time of reactants is in the range of about 0.5 and 100 seconds.

The following examples describe the procedures used for the preparing various catalysts employed in the examples which follow.

EXAMPLE A

Preparation of 1 Weight Percent Ruthenium on Iron Oxide

Powdered and meshed iron oxide (99 g) of uniform particle size distribution of about 0.2 mm was dried at 120° C. in an oven under nitrogen atmosphere overnight and then cooled to room temperature. To this was added a solution of ruthenium nitrosyl nitrate (Heraeus) (3.14 g) in distilled water (32 ml). The resulting slurry was dried in an oven gradually heated to 110° C. (>2 hours, 10° C./min). The impregnated catalyst mixture was then calcined at 500° C. (6 hours, 1° C./min).

EXAMPLE B

Preparation of 3 Weight Percent Ruthenium on Iron Oxide

The procedures of Example A were substantially repeated except for utilizing a solution of ruthenium nitrosyl nitrate (Heraeus) (9.42 g) in distilled water (96 ml) and 97 grams of iron oxide.

EXAMPLE C

Preparation of 5 Weight Percent Iron on High Purity, Low Surface Area Silica

Powdered and meshed high purity, low surface area silica (95 g) of uniform particle size distribution of about 0.2 mm was dried at 120° C. in an oven under nitrogen atmosphere overnight and then cooled to room temperature. To this was added a solution of iron nitrate nonahydrate (Alfa Aesar) (36.2 g) in distilled water (36 ml). The resulting slurry was dried in an oven gradually heated to 110° C. (>2 hours, 10° C./min). The impregnated catalyst mixture was then calcined at 500° C. (6 hours, 1° C./min).

EXAMPLE D

Preparation of 5 Weight Percent Tin and 0.5 Weight Percent Ruthenium on High Purity Low, Surface Area Silica Powdered and meshed high purity, low surface area silica (94 g) of uniform particle size distribution of about 0.2 mm was dried at 120° C. in an oven under nitrogen atmosphere overnight and then cooled to room temperature. To this was added a solution of tin oxalate (Alfa Aesar) (8.7 g) in dilute nitric acid (1N 45 ml). The resulting slurry was dried in an oven gradually heated to 110° C. (>2 hours, 10° C./min). The impregnated catalyst mixture was then calcined at 500° C. (6 hours, 1° C./min). To this calcined and cooled material was added a solution of ruthenium nitrosyl nitrate (Heraeus) (1.57 g) in distilled water (16 ml). The resulting slurry was dried in an oven gradually heated to 110° C. (>2 hours, 10° C./min). The impregnated catalyst mixture was then calcined at 500° C. (6 hours, 1° C./min).

EXAMPLE E

Preparation of 1 Weight Percent Ruthenium and 5 Weight Percent Iron on High Purity Low, Surface Area Silica Powdered and meshed high purity low surface area silica (94 g) of uniform particle size distribution of about 0.2 mm was dried at 120° C. in an oven under nitrogen atmosphere overnight and then cooled to room temperature. To this was added a solution of ruthenium nitrosyl nitrate (Heraeus) (3.14 g) in distilled water (32 ml). The resulting slurry was dried in an oven gradually heated to 110° C. (>2 hours, 10° C./min). The impregnated catalyst mixture was then calcined at 500° C. (6 hours, 1° C./min). To this calcined and cooled material was added a solution of iron nitrate nonahydrate (Alfa Aesar) (36.2 g) in distilled water (36 ml). The resulting slurry was dried in an oven gradually heated to 110° C. (>2 hours, 10° C./min). The impregnated catalyst mixture was then calcined at 500° C. (6 hours, 1° C./min).

EXAMPLE F

Preparation of 5 Weight Percent Iron and 1 Weight Percent Platinum on High Purity, Low Surface Area Silica Powdered and meshed high purity, low surface area silica (94 g) of uniform particle size distribution of about 0.2 mm was dried at 120° C. in an oven under nitrogen atmosphere overnight and then cooled to room temperature. To this was added a solution of iron nitrate nonahydrate (Alfa Aesar) (36.2 g) in distilled water (36 ml). The resulting slurry was dried in an oven gradually heated to 110° C. (>2 hours, 10° C./min). The impregnated catalyst mixture was then calcined at 500° C. (6 hours, 1° C./min). To this calcined and cooled material was added a solution of platinum nitrate (Chempur) (1.64 g) in distilled water (16 ml). The resulting slurry was dried in an oven gradually heated to 110° C. (>2 hours, 10° C./min). The impregnated catalyst mixture was then calcined at 500° C. (6 hours, 1° C./min).

EXAMPLE G

Preparation of 1 Weight Percent Platinum and 5 Weight Percent Tin on High Purity, Low Surface Area Silica Powdered and meshed high purity, low surface area silica (94 g) of uniform particle size distribution of about 0.2 mm was dried at 120° C. in an oven under nitrogen atmosphere overnight and then cooled to room temperature. To this was added a solution of platinum nitrate (Chempur) (1.64 g) in distilled water (16 ml) and a solution of tin oxalate (Alfa Aesar) (8.7 g) in dilute nitric acid (1N, 43.5 ml). The resulting slurry was dried in an oven gradually heated to 110° C. (>2 hours, 10° C./min.). The impregnated catalyst mixture was then calcined at 500° C. (6 hours, 1° C./min).

EXAMPLE H

Preparation of 1 Weight Percent Palladium, 1 Weight Percent Gold and 5 Weight Percent Potassium Acetate on High Purity, Low Surface Area Silica The procedures of Example D were substantially repeated except for utilizing a solution of palladium nitrate (Heraeus) (2.17 g) in distilled water (22 ml), a solution of gold(III) hydroxide (Alfa Aesar) (1.26 g) and potassium hydroxide (0.28 g) in distilled water (10 ml), a solution of potassium acetate (Sigma) (5 g) in distilled water (10 ml) and 93 grams of silica. The catalyst was sequentially impregnated first with palladium and then with gold and finally with potassium acetate.

EXAMPLE I

Preparation of 1 Weight Percent Palladium, 5 Weight Percent Copper and 5 Weight Percent Potassium Acetate on High Purity, Low Surface Area Silica The procedures of Example D were substantially repeated except for utilizing a solution of palladium nitrate (Heraeus) (2.17 g) in distilled water (22 ml), a solution of copper nitrate trihydrate (Alfa Aesar) (19 g) in distilled water (20 ml), a solution of potassium acetate (Sigma) (5 g) in distilled water (10 ml) and 89 grams of silica. The catalyst was sequentially impregnated first with copper and then with palladium and finally with potassium acetate.

EXAMPLE J

Preparation of 1 Weight Percent Palladium and 5 Weight Percent Copper on Carbon

The procedures of Example D were substantially repeated except for utilizing a solution of palladium nitrate (Heraeus) (2.17 g) in distilled water (22 ml), a solution of copper nitrate trihydrate (Alfa Aesar) (19 g) in distilled water (20 ml) and 94 grams of carbon. The catalyst was sequentially impregnated first with copper and then with palladium.

EXAMPLE K

Preparation of 1 Weight Percent Palladium and 5 Weight Percent Iron on High Purity, Low Surface Area Silica The procedures of Example D were substantially repeated except for utilizing a solution of palladium nitrate (Heraeus) (2.17 g) in distilled water (22 ml), a solution of iron nitrate nonahydrate (Alfa Aesar) (36.2 g) in distilled water (30 ml) and 94 grams of silica. The catalyst was sequentially impregnated first with iron and then with palladium.

EXAMPLE L

Preparation of 5 Weight Percent Iron and 5 Weight Percent Cobalt on High Purity, Low Surface Area Silica The procedures of Example D were substantially repeated except for utilizing a solution of iron nitrate nonahydrate (Alfa Aesar) (36.2 g) in distilled water (30 ml), a solution of cobalt nitrate hexahydrate (24.7 g) in distilled water (25 ml) and 90 grams of silica. The catalyst was sequentially impregnated first with iron and then with cobalt.

EXAMPLE M

Preparation of 5 Weight Percent Copper and 5 Weight Percent Molybdenum on High Purity, Low Surface Area Silica The procedures of Example D were substantially repeated except for utilizing a solution of copper nitrate trihydrate (Alfa Aesar) (19 g) in distilled water (20 ml), a solution of ammonium heptamolybdate hexahydrate (Sigma) (9.5 g) in distilled water (65 ml) and 90 grams of silica. The catalyst was sequentially impregnated first with copper and then with molybdenum.

EXAMPLE N

Preparation of 5 Weight Percent Tin and 1 Weight Percent Ruthenium on High Purity, Low Surface Area Silica The procedures of Example D were substantially repeated except for utilizing a solution of tin oxalate (Alfa Aesar) (8.7 g) in dilute nitric acid (1N, 43.5 ml), a solution of ruthenium nitrosyl nitrate (Heraeus) (3.14 g) in distilled water (32 ml) and 94 grams of silica. The catalyst was co-impregnated with tin and ruthenium.

EXAMPLE O

Preparation of 1 Weight Percent Palladium on Iron Oxide

The procedures of Example D were substantially repeated except for utilizing a solution of palladium nitrate (Heraeus) (2.17 g) in distilled water (22 ml) and 99 grams of iron oxide.

Gas Chromatographic (GC) Analysis of the Products

The analysis of the products was carried out by online GC. A three channel compact GC equipped with one flame ionization detector (FID) and 2 thermal conducting detectors (TCDs) was used to analyze the reactants and products. The front channel was equipped with an FID and a CP-Sil 5 (20 m)+WaxFFap (5 m) column and was used to quantify:
Acetaldehyde
Ethanol
Acetone
Methyl acetate
Vinyl acetate
Ethyl acetate
Acetic acid
Ethylene glycol diacetate
Ethylene glycol
Ethylidene Diacetate
Paraldehyde The middle channel was equipped with a TCD and Porabond Q column and was used to quantify:
$CO_2$
Ethylene
Ethane The back channel was equipped with a TCD and Molsieve 5A column and was used to quantify:
Helium
Hydrogen
Nitrogen
Methane
Carbon monoxide Prior to reactions, the retention time of the different components was determined by spiking with individual compounds and the GCs were calibrated either with a calibration gas of known composition or with liquid solutions of known compositions. This allowed the determination of the response factors for the various components.

EXAMPLE 1

The catalyst utilized was 1 weight percent ruthenium on iron oxide prepared in accordance with the procedure of Example A.

In a tubular reactor made of stainless steel, having an internal diameter of 30 mm and capable of being raised to a controlled temperature, there are arranged 50 ml of 1 weight percent ruthenium supported on iron oxide. The length of the catalyst bed after charging was approximately about 70 mm. Prior to the reaction the catalyst was reduced in situ by heating at a rate of 2° C./min to a final temperature of 400° C. Then, 5 mol % hydrogen in nitrogen was introduced to the catalyst chamber at a gas hourly space velocity (GHSV) of 7500 l $h^{-1}$. After reduction, the catalyst was cooled to reaction temperature of 350° C. by continuing the gas flow of 5 mol % hydrogen in nitrogen. Once the reaction temperature was stabilized at 350° C., the hydrogenation of acetic acid was begun as follows.

A feed liquid was comprised essentially of acetic acid. The reaction feed liquid was evaporated and charged to the reactor along with hydrogen and helium as a carrier gas with an average combined gas hourly space velocity (GHSV) of about 2500 $hr^{-1}$ at a temperature of about 350° C. The resulting feed stream contained a mole percent of acetic acid from about 4.4% to about 13.8% and the mole percent of hydrogen from about 14% to about 77%. A portion of the vapor effluent was passed through a gas chromatograph for analysis of the contents of the effluents. The selectivity to acetaldehyde was 60% at a conversion of acetic acid of 50%.

EXAMPLE 2

The catalyst utilized was 5 weight percent iron on silica prepared in accordance with the procedure of Example C.

The procedure as set forth in Example 1 was substantially repeated with an average combined gas hourly space velocity (GHSV) of 2,500 $hr^{-1}$ of the feed stream of the vaporized acetic acid and hydrogen ($H_2$ to acetic acid mole ratio of 5) at a temperature of 350° C. A portion of the vapor effluent is passed through a gas chromatograph for analysis of the contents of the effluents. The acetic acid conversion was 75% and acetaldehyde selectivity was 70%.

EXAMPLE 3

The catalyst utilized was 0.5 weight percent ruthenium and 5 weight percent tin on silica prepared in accordance with the procedure of Example D.

The procedure as set forth in Example 1 is substantially repeated with an average combined gas hourly space velocity (GHSV) of 10,000 $hr^{-1}$ of the feed stream of the vaporized acetic acid and hydrogen ($H_2$ to acetic acid mole ratio of 5) at a temperature of 250° C. and at a pressure of 1 bar. A portion of the vapor effluent is passed through a gas chromatograph for analysis of the contents of the effluents. The acetic acid conversion was 4% and acetaldehyde selectivity was 91%. The other products formed were ethane (1%) and ethanol (8%).

EXAMPLE 4

The catalyst utilized was 1 weight percent ruthenium and 5 weight percent iron on silica prepared in accordance with the procedure of Example E.

The procedure as set forth in Example 1 was substantially repeated with an average combined gas hourly space velocity (GHSV) of 2,500 $hr^{-1}$ of the feed stream of the vaporized acetic acid and hydrogen ($H_2$ to acetic acid mole ratio of 5) at a temperature of 300° C. A portion of the vapor effluent is passed through a gas chromatograph for analysis of the contents of the effluents. The acetic acid conversion is 35% and acetaldehyde selectivity is about 70%.

EXAMPLE 5

The catalyst utilized was 1 weight percent platinum and 5 weight percent iron on High Purity, Low Surface Area Silica prepared in accordance with the procedure of Example F.

The procedure as set forth in Example 1 was substantially repeated with an average combined gas hourly space velocity (GHSV) of 2,500 $hr^{-1}$ of the feed stream of the vaporized acetic acid and hydrogen ($H_2$ to acetic acid mole ratio of 5) at a temperature of 350° C. and at a pressure of 1 bar. A portion of the vapor effluent is passed through a gas chromatograph for analysis of the contents of the effluents. The acetic acid conversion was 65% and acetaldehyde selectivity is 60%. The other products formed were carbon dioxide (6%) and ethyl acetate (9%).

EXAMPLE 6

The catalyst utilized was 0.5 weight percent platinum and 5 weight percent tin on silica prepared in accordance with the procedure of Example G.

The procedure as set forth in Example 1 was substantially repeated with an average combined gas hourly space velocity (GHSV) of 2,500 hr$^{-1}$ of the feed stream of the vaporized acetic acid and hydrogen ($H_2$ to acetic acid mole ratio of 5) at a temperature of 350° C. and at a pressure of 1 bar. A portion of the vapor effluent is passed through a gas chromatograph for analysis of the contents of the effluents. The acetic acid conversion was 85% and acetaldehyde selectivity was 65%. The other products formed were methane (4%) and ethyl acetate (9%).

EXAMPLE 7

The catalyst utilized was a commercially available Co/Fe catalyst containing 17.4 weight percent cobalt and 4.8 weight percent iron on silica The procedure as set forth in Example 1 is substantially repeated with an average combined gas hourly space velocity (GHSV) of 2,500 hr$^{-1}$ of the feed stream of the vaporized acetic acid and hydrogen at a temperature of 350° C. A portion of the vapor effluent is passed through a gas chromatograph for analysis of the contents of the effluents. The acetic acid conversion is about 65% and acetaldehyde selectivity is 75%.

EXAMPLE 8

The catalyst utilized was 1 weight percent palladium, 1 weight percent gold and 5 weight percent potassium acetate on silica prepared in accordance with the procedure of Example H.

The procedure as set forth in Example 1 was substantially repeated with an average combined gas hourly space velocity (GHSV) of 10,000 hr$^{-1}$ of the feed stream of the vaporized acetic acid and hydrogen ($H_2$ to acetic acid mole ratio of 5) at a temperature of 250° C. and at a pressure of 1 bar. A portion of the vapor effluent is passed through a gas chromatograph for analysis of the contents of the effluents. The acetic acid conversion was 5% and acetaldehyde selectivity was 98.5%. The other products formed were ethane (1%) and ethanol (0.5%).

EXAMPLE 9

The catalyst utilized was 1 weight percent palladium, 5 weight percent copper and 5 weight percent potassium acetate on silica prepared in accordance with the procedure of Example I.

The procedure as set forth in Example 1 was substantially repeated with an average combined gas hourly space velocity (GHSV) of 10,000 hr$^{-1}$ of the feed stream of the vaporized acetic acid and hydrogen ($H_2$ to acetic acid mole ratio of 5) at a temperature of 250° C. and at a pressure of 1 bar. A portion of the vapor effluent is passed through a gas chromatograph for analysis of the contents of the effluents. The acetic acid conversion was 2% and acetaldehyde selectivity was 97.5%. The other product formed was ethane (2.5%).

EXAMPLE 10

The catalyst utilized was 1 weight percent palladium and 5 weight percent copper on carbon prepared in accordance with the procedure of Example J.

The procedure as set forth in Example 1 was substantially repeated with an average combined gas hourly space velocity (GHSV) of 10,000 hr$^{-1}$ of the feed stream of the vaporized acetic acid and hydrogen ($H_2$ to acetic acid mole ratio of 5) at a temperature of 250° C. and at a pressure of 1 bar. A portion of the vapor effluent is passed through a gas chromatograph for analysis of the contents of the effluents. The acetic acid conversion was 1% and acetaldehyde selectivity was 97%. The other product formed was ethane (3%).

EXAMPLE 11

The catalyst utilized was 1 weight percent palladium and 5 weight percent iron on silica prepared in accordance with the procedure of Example K.

The procedure as set forth in Example 1 was substantially repeated with an average combined gas hourly space velocity (GHSV) of 10,000 hr$^{-1}$ of the feed stream of the vaporized acetic acid and hydrogen ($H_2$ to acetic acid mole ratio of 5) at a temperature of 250° C. and at a pressure of 1 bar. A portion of the vapor effluent is passed through a gas chromatograph for analysis of the contents of the effluents. The acetic acid conversion was 9% and acetaldehyde selectivity was 96%. The other products formed were ethane (0.6%) and ethanol (3.6%).

EXAMPLE 12

The catalyst utilized was 5 weight percent iron and 5 weight percent cobalt on silica prepared in accordance with the procedure of Example L.

The procedure as set forth in Example 1 was substantially repeated with an average combined gas hourly space velocity (GHSV) of 10,000 hr$^{-1}$ of the feed stream of the vaporized acetic acid and hydrogen ($H_2$ to acetic acid mole ratio of 5) at a temperature of 250° C. and at a pressure of 1 bar. A portion of the vapor effluent is passed through a gas chromatograph for analysis of the contents of the effluents. The acetic acid conversion was 11% and acetaldehyde selectivity was 95%. The other products formed were ethane (1%) and ethanol (4%).

EXAMPLE 13

The catalyst utilized was 5 weight percent iron and 5 weight percent cobalt on silica prepared in accordance with the procedure of Example L.

The procedure as set forth in Example 1 was substantially repeated with an average combined gas hourly space velocity (GHSV) of 2,500 hr$^{-1}$ of the feed stream of the vaporized acetic acid and hydrogen ($H_2$ to acetic acid mole ratio of 5) at a temperature of 350° C. and at a pressure of 1 bar. A portion of the vapor effluent is passed through a gas chromatograph for analysis of the contents of the effluents. The acetic acid conversion was 75% and acetaldehyde selectivity was 70%. The other products formed were methane (4%) and carbon dioxide (3%).

EXAMPLE 14

The catalyst utilized was 5 weight percent copper and 5 weight percent molybdenum on silica prepared in accordance with the procedure of Example M.

The procedure as set forth in Example 1 was substantially repeated with an average combined gas hourly space velocity (GHSV) of 2,500 hr$^{-1}$ of the feed stream of the vaporized acetic acid and hydrogen ($H_2$ to acetic acid mole ratio of 5) at a temperature of 350° C. and at a pressure of 1 bar. A portion of the vapor effluent is passed through a gas chromatograph for analysis of the contents of the effluents. The acetic acid conversion was 10% and acetaldehyde selectivity was 90%. The other products formed were ethane (1.5%) and acetone (6.6%).

EXAMPLE 15

The catalyst utilized was 1 weight percent ruthenium and 5 weight percent tin on silica prepared in accordance with the procedure of Example N.

The procedure as set forth in Example 1 was substantially repeated with an average combined gas hourly space velocity (GHSV) of 2,500 $hr^{-1}$ of the feed stream of the vaporized acetic acid and hydrogen ($H_2$ to acetic acid mole ratio of 5) at a temperature of 350° C. and at a pressure of 1 bar. A portion of the vapor effluent is passed through a gas chromatograph for analysis of the contents of the effluents. The acetic acid conversion was 60% and acetaldehyde selectivity was 78%. The other products formed were methane (6%) and ethanol (12%).

EXAMPLE 16

The catalyst utilized was 1 weight percent palladium on iron oxide prepared in accordance with the procedure of Example O.

The procedure as set forth in Example 1 was substantially repeated with an average combined gas hourly space velocity (GHSV) of 10,000 $hr^{-1}$ of the feed stream of the vaporized acetic acid and hydrogen ($H_2$ to acetic acid mole ratio of 5) at a temperature of 350° C. and at a pressure of 15 bar. A portion of the vapor effluent is passed through a gas chromatograph for analysis of the contents of the effluents. The acetic acid conversion was 66% and acetaldehyde selectivity was 59%. The other products formed were carbon dioxide (4%) and ethanol (18%).

EXAMPLE 17

The catalyst utilized was commercially available copper-aluminum catalyst sold under the name of T-4489 from Sud Chemie.

The procedure as set forth in Example 1 was substantially repeated with an average combined gas hourly space velocity (GHSV) of 2,500 $hr^{-1}$ of the feed stream of the vaporized acetic acid and hydrogen ($H_2$ to acetic acid mole ratio of 5) at a temperature of 350° C. and at a pressure of 1 bar. A portion of the vapor effluent is passed through a gas chromatograph for analysis of the contents of the effluents. The acetic acid conversion was 88% and acetaldehyde selectivity was 51%. The other products formed were carbon dioxide (5%) and ethanol (16%).

Comparative Examples 1A-4A

These examples illustrate the reaction of acetic acid and hydrogen over a variety of catalysts wherein either no acetaldehyde was formed and/or very low selectivity to acetaldehyde was observed at low conversions of acetic acid.

In all of these examples, the procedure as set forth in Example 1 was substantially followed with the exception of using different catalysts as listed in Table 1. The reaction temperature and selectivity to acetaldehyde and other products are also tabulated in Table 1.

TABLE 1

Acetic Acid Conversion and Selectivities for Comparative Examples

| Example | Catalyst | Acetaldehyde selectivity (%) | Acetic acid conversion (%) | Other products |
|---|---|---|---|---|
| 1A | 5 wt % Cu/$Fe_2O_3$ | 31 | 100 | ethylene-16%, ethane-15%, ethyl acetate-4%, $CO_2$-5% |
| 2A | 5 wt % Co/H-ZSM-5 | 44 | 3 | ethylene-28%, ethane-28% |
| 3A | 5 wt % Co 5 Wt % Ru/$SiO_2$ | 78 | 4 | ethylene-14%, ethane-8% |
| 4A | 5 wt % Co/Carbon | 0 | 2 | Ethylene - 12% acetone-8%, methane-47%, ethane-5% |

While the invention has been illustrated in connection with particular examples, modifications to these examples within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary.

What is claimed is:

1. A process for selective and direct formation of acetaldehyde from acetic acid comprising: contacting a feed stream containing acetic acid and hydrogen at an elevated temperature with a hydrogenating catalyst carried on a support, said hydrogenating catalyst comprising copper and an additional metal selected from the group consisting of tin, aluminum, potassium, cobalt, molybdenum, tungsten and vanadium.

2. The process according to claim 1, wherein the additional metal is molybdenum.

3. The process according to claim 1, wherein the loading level of molybdenum is about 5.0 weight percent.

4. The process according to claim 1, wherein the loading level of copper is about 5.0 weight percent.

5. The process according to claim 1, wherein the support is selected from the group consisting of silica, titania, alumina, zirconia, calcium silicate, titania-silica, zirconia-silica and combinations thereof.

6. The process according to claim 1, wherein the hydrogenation to acetaldehyde is carried out in the vapor phase and at a temperature in the range of about 250° C. to 350° C.

7. The process according to claim 1, wherein the selectivity to acetaldehyde based on acetic acid consumed is at least 60 percent.

8. The process according to claim 1, wherein the pressure of the reaction zone is about 1 atmosphere absolute.

9. A hydrogenating catalyst for producing acetaldehyde comprising:
 (a) from 0.5 to 20.0 wt. % of iron;
 (b) a second metal selected from the group consisting of ruthenium, platinum, cobalt, and palladium; and
 (c) a support chosen from the group consisting of silica, titania, alumina, zirconia, calcium silicate, titania-silica, zirconia-silica, and combinations thereof;
 provided that the second metal is present in an amount of 1 wt. % or less when the second metal is selected from the group consisting of ruthenium, platinum and palladium; and
 further provided that the second metal is present in an amount of 20 wt. % or less when the second metal is cobalt.

* * * * *